United States Patent
Presty

(10) Patent No.: US 8,318,797 B2
(45) Date of Patent: Nov. 27, 2012

(54) COMPOSITION AND METHODS FOR THE PROTECTION OF HAIR FROM TREATED POOL WATER

(76) Inventor: S. Katharine Presty, Huntersville, NC (US)

( * ) Notice: Subject to any disclaimer, the term of this patent is extended or adjusted under 35 U.S.C. 154(b) by 346 days.

(21) Appl. No.: 12/608,233

(22) Filed: Oct. 29, 2009

(65) Prior Publication Data

US 2010/0113588 A1     May 6, 2010

Related U.S. Application Data

(60) Provisional application No. 61/109,869, filed on Oct. 30, 2008.

(51) Int. Cl.
*A61K 31/335* (2006.01)
*A61K 31/197* (2006.01)
*A61K 31/05* (2006.01)
*A61K 31/015* (2006.01)
*A61K 47/32* (2006.01)
*A61K 7/06* (2006.01)
*A61P 39/06* (2006.01)

(52) U.S. Cl. ........ 514/458; 514/562; 514/731; 514/734; 514/763; 514/772; 514/772.4; 514/772.5; 424/70.51

(58) Field of Classification Search .................. None
See application file for complete search history.

(56) References Cited

U.S. PATENT DOCUMENTS 6,013,250 A * 1/2000 Cannell et al. ............. 424/70.51
2007/0196400 A1 * 8/2007 Raschke et al. ............. 424/401

FOREIGN PATENT DOCUMENTS

JP    2007039410 A * 2/2007

* cited by examiner

*Primary Examiner* — Ernst Arnold
*Assistant Examiner* — Hong Yu
(74) *Attorney, Agent, or Firm* — Withers & Keys, LLC

(57) ABSTRACT

Compositions for treating hair are disclosed. Methods of making and using compositions for treating hair are also disclosed.

19 Claims, No Drawings

COMPOSITION AND METHODS FOR THE PROTECTION OF HAIR FROM TREATED POOL WATER

CROSS-REFERENCE TO RELATED APPLICATIONS

This patent application claims the benefit of priority to U.S. provisional patent application Ser. No. 61/109,869 entitled "COMPOSITIONS AND METHOD FOR PROTECTION OF HAIR FROM TREATED POOL WATER" filed on Oct. 30, 2008, the subject matter of which is incorporated herein in its entirety.

FIELD OF THE INVENTION

The present invention is directed to compositions for treating hair. The present invention is further directed to methods of making and using compositions for treating hair.

BACKGROUND OF THE INVENTION

The use of chlorine, and to a lesser degree, bromine, and saline, to disinfect both indoor and outdoor swimming pools has been used for some time in order to reduce micro-organism populations. Halogen-containing compounds are used as a result of their rapid in vivo microbiocidal activity due to their strong oxidizing potential in the presence of organic residues, which is essential for rapid reduction of pathogens, which can promote the induction and spread of disease. Chlorine is by far the most widely used disinfectant due primarily to its cost effectiveness and acceptable safety profile. The chlorine compounds most effectively employed consist of sodium hypochlorite, calcium hypochlorite and chlorinated isocyanurates. Sodium hypochlorite is preferred as a result of its lower cost water solubility and ease of dispersion together with easier control of pH requirements for optimal microbiocidal activity. To this effect sodium hypochlorite dissociates in water into hypochlorous acid together with sodium and hypochlorite ions depending upon the pH of the water.

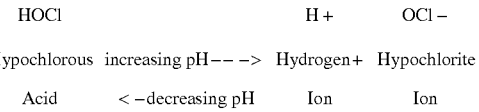

| HOCl | | H+ | OCl− |
|---|---|---|---|
| Hypochlorous | increasing pH ---> | Hydrogen+ | Hypochlorite |
| Acid | < −decreasing pH | Ion | Ion |

The hypochlorous acid (HA) is the species, which is the oxidant and micro biocide, and therefore, based on the above reaction, exhibits a maximum concentration at neutral pH or in actuality 7.2 to 7.8, These ranges are critical as at 7.2, 66% exists as HA compared to 33% at 7.8, At acidic pH, the chlorine is rapidly lost and at high pH the HA rapidly falls as the equilibrium favors the inactive ionic dissociation as shown above. Based on the foregoing, the advantages of using a halogen and particularly chlorine are obvious, however, the potent oxidizing potential presents deleterious effects to hair. This is evident to both short and long term exposure as oxidants of this type exhibit a rapid electrophilic attack (i.e., draw electrons) from any organic substance, such as hair, lowering its tensile strength, which promotes cuticle damage. This exposes the interior hair morphology to further electrophilic attack leading to free radical induced cellular damage within the cortex. In summary, the least of these problems are also cosmetic, leaving healthy hair damaged, dry/stiff, and subject to breakage in addition to snarling and tangling.

Hair treatment products have been designed for consumer use to rectify and, or mitigate the foregoing consisting of post-treatment with shampoo and conditioners containing antioxidants or reducing agents to remove residual chlorine from hair after swimming. However, these products have been, for the most part, ineffective mainly as a result of the rapid oxidation effects to hair as described above. As a result, the post-treatments described above do not address the irreversible problem of deleterious effects encountered while swimming.

There exists a need in the art for a pre-treatment of hair and scalp prior to immersion in the treated pool arena.

SUMMARY OF THE INVENTION

The present invention addresses the need in the art of compositions and methods of pre-treatment for hair prior to oxidation exposure such as encountered in treated pools (e.g., a chlorinated swimming pool). Thus it is an object of the present invention to provide compositions for pre-treatment of hair prior to exposure to deleterious oxidants. It is also an object of the present invention to provide a method for protecting hair from oxidants and harmful residues encountered in a treated pool environment. It is still further an object of this invention to provide cosmetically acceptable products, which are safe, cost-effective, and consumer friendly, and which after use in a treated pool, leave hair healthy and manageable.

The use of an effective pre-treatment regimen has numerous advantages. Effective protection via the disclosed pre-treating does not permit exposure of treated hair to deleterious chemical agents, such as oxidants. Thus, the instantaneous damage to the exterior and interior of hair are nonexistent when pre-treated according to the present invention. This includes both cosmetic homeostatic and structural damage, such as depletion of the cuticle and cellular damage within the cortex. The hair maintains its natural oil composition (sebum) (i.e., while swimming) as opposed to oxidization leading to the generation of free radicals in sebum lipids, which can become comedogenic to surrounding skin mucosa, i.e. scalp and forehead. Thus as opposed to post-treatment with compositions containing reducing agents, pre-treatment prevents the damage from happening, thereby eliminating or reducing the need for ineffective extensive post remedies.

Accordingly, the present invention is directed to hair pre-treatment compositions suitable for protection of hair from exposure to Oxidizing agents. In one exemplary embodiment, the hair pre-treatment composition of the present invention comprises at least one hydrophilic cationic polymer; at least one lipophilic nonionic polymer; one or more water-soluble antioxidants or reducing agents; and one or more oil-soluble antioxidants or reducing agents. In some exemplary embodiments, the hair pre-treatment composition comprises at least one hydrophilic cationic polymer in the form of a guar hydroxypropyltrimonium chloride (GHPTC); at least one lipophilic nonionic polymer in the form of (i) a polyvinyl stearyl ether, (ii) a vinylpyrrolidone-eicosene copolymer, or (iii) a combination of (i) and (ii); one or more water-soluble antioxidants or reducing agents in the form of cysteine, methionine, BHT, BHA, a polyphenol of plant origin, or any mixture thereof; and one or more oil-soluble antioxidants or reducing agents in the form of a tocopherol, a tocotrienol, beta carotene, or any mixture thereof.

In another exemplary embodiment, the hair pre-treatment composition of the present invention comprises at least one lipophilic nonionic polymer comprising (i) a polyvinyl stearyl ether, (ii) a vinylpyrrolidone-eicosene copolymer, or (iii) a combination of (i) and (ii). The exemplary hair pre-treatment composition may further comprise one or more of (i) at least one hydrophilic cationic polymer comprising guar hydroxypropyltrimonium chloride (GHPTC), a cationic cellulosic polymer, a diallyl dimethyl ammonium chloride/acrylamide copolymer, or any combination thereof; (ii) one or more water-soluble antioxidants or reducing agents comprising cysteine, methionine, BHT, BHA, a polyphenol of plant origin, or any mixture thereof; (iii) one or more oil-soluble antioxidants or reducing agents comprising a tocopherol, a tocotrienol, beta carotene, or any mixture thereof; and (iv) one or more optional cosmetic base materials such as a humectant, a fragrance, a pH control agent, a buffer, or a combination thereof.

In yet another exemplary embodiment, the hair pre-treatment composition of the present invention comprises at least one hydrophilic cationic polymer, wherein the at least one hydrophilic cationic polymer comprises guar hydroxypropyltrimonium chloride (GHPTC); at least one lipophilic nonionic polymer, wherein the at least one lipophilic nonionic polymer comprises (i) a polyvinyl stearyl ether, (ii) a vinylpyrrolidone-eicosene copolymer, or (iii) a combination of (i) and (ii); one or more water-soluble antioxidants or reducing agents, wherein the one or more water-soluble antioxidants or reducing agents comprises cysteine, methionine, or any mixture thereof; and one or more oil-soluble antioxidants or reducing agents, wherein the one or more oil-soluble antioxidants or reducing agents comprises a tocopherol, a tocotrienol, beta carotene, or any mixture thereof.

The present invention is also directed to methods of making and using hair pre-treatment compositions suitable for protecting hair from exposure to oxidizing agents. In one exemplary embodiment, the method of making a hair pre-treatment composition of the present invention comprises mixing (i) at least one hydrophilic cationic polymer; (ii) at least one lipophilic nonionic polymer; (iii) one or more water-soluble antioxidants or reducing agents; and (iv) one or more oil-soluble antioxidants or reducing agents. In some exemplary embodiments, the method of making a hair pre-treatment composition comprises mixing (1) at least one hydrophilic cationic polymer in the form of a guar hydroxypropyltrimonium chloride (GHPTC); (2) at least one lipophilic nonionic polymer in the form of (i) a polyvinyl stearyl ether, (ii) a vinylpyrrolidone-eicosene copolymer, or (iii) a combination of (i) and (ii); (3) one or more water-soluble antioxidants or reducing agents in the form of cysteine, methionine, BHT, BHA, a polyphenol of plant origin, or any mixture thereof; and (4) one or more oil-soluble antioxidants or reducing agents in the form of a tocopherol, a tocotrienol, beta carotene, or any mixture thereof.

In other exemplary embodiments, the method of making a hair pre-treatment composition comprises forming a hair pre-treatment composition comprising at least one lipophilic nonionic polymer comprising (i) a polyvinyl stearyl ether, (ii) a vinylpyrrolidone-eicosene copolymer, or (iii) a combination of (i) and (ii). In this exemplary method, the method of making a hair pre-treatment composition may further comprise incorporating one or more of the following components into the lipophilic nonionic polymer-containing composition: (i) at least one hydrophilic cationic polymer comprising guar hydroxypropyltrimonium chloride (GHPTC), a cationic cellulosic polymer, a diallyl dimethyl ammonium chloride/acrylamide copolymer, or any combination thereof; (ii) one or more water-soluble antioxidants or reducing agents comprising cysteine, methionine, BHT, BHA, a polyphenol of plant origin, or any mixture thereof; (iii) one or more oil-soluble antioxidants or reducing agents comprising a tocopherol, a tocotrienol, beta carotene, or any mixture thereof; and (iv) one or more optional cosmetic base materials such as a humectant, a fragrance, a pH control agent, a buffer, or a combination thereof.

In yet other exemplary embodiments, the method of making a hair pre-treatment composition comprises forming a hair pre-treatment composition comprising at least one hydrophilic cationic polymer, wherein the at least one hydrophilic cationic polymer comprises guar hydroxypropyltrimonium chloride (GHPTC); at least one lipophilic nonionic polymer, wherein the at least one lipophilic nonionic polymer comprises (i) a polyvinyl stearyl ether, (ii) a vinylpyrrolidone-eicosene copolymer, or (iii) a combination of (i) and (ii); one or more water-soluble antioxidants or reducing agents, wherein the one or more water-soluble antioxidants or reducing agents comprises cysteine, methionine, or any mixture thereof; and one or more oil-soluble antioxidants or reducing agents, wherein the one or more oil-soluble antioxidants or reducing agents comprises a tocopherol, a tocotrienol, beta carotene, or any mixture thereof.

Methods of using the disclosed hair pre-treatment compositions comprise applying a given hair pre-treatment composition to hair prior to exposing the hair to an oxidizing environment, such as a chlorinated swimming pool. In one exemplary embodiment, the method of using a hair pre-treatment composition comprises applying a hair pre-treatment composition to hair, wherein the hair pre-treatment composition comprises one or more of the following components: (i) at least one hydrophilic cationic polymer; (ii) at least one lipophilic nonionic polymer; (iii) one or more water-soluble antioxidants or reducing agents; (iv) one or more oil-soluble antioxidants or reducing agents; and (v) one or more optional cosmetic base materials such as a dye, a fragrance, etc. Exemplary methods of using a disclosed hair pre-treatment composition may further comprise one or more additional steps such as exposing the treated hair to an oxidizing environment (e.g., a chlorinated swimming pool); rinsing the treated hair prior to and/or after exposure to the oxidizing environment; shampooing the treated hair to remove at least a portion of the hair pre-treatment composition; conditioning the hair following or during the shampooing step; and drying the hair.

The present invention is further directed to treated hair comprising hair coated with any of the hair pre-treatment compositions of the present invention.

The present invention is even further directed to method of doing business, wherein the method of doing business comprises offering for sale any of the hair pre-treatment compositions of the present invention. Exemplary methods of doing business may comprise offering for sale a given the hair pre-treatment composition of the present invention alone or in a hair treatment kit containing other hair treatment products such as a shampoo, a conditioner, or a combination thereof.

These and other features and advantages of the present invention will become apparent after a review of the following detailed description of the disclosed embodiments and the appended claims.

DETAILED DESCRIPTION

The present invention is directed to a variety of hair pre-treatment compositions. In some embodiments, the hair pre-treatment compositions comprise (or consist essentially of, or consist of) a combination of (I) one or more hydrophilic water-soluble polymers in combination with (2) one or more nonionic lipophilic oil soluble polymers together with selected (3) water- and (4) oil-soluble antioxidants or reducing agents in (5) an acceptable cosmetic base. The hair pre-treatment compositions and method of use are effective for protecting hair from damage caused by antibacterial and/or oxidizing agents normally employed in treated pools (e.g., swimming pools). These consist of, but are not limited to, ionic salts containing an oxidized ionic species, such as halogens, consisting of mainly chlorine- and bromine-containing oxidizing agents such as sodium hypochlorite, etc., oxygen bleaches such as sodium perborate, and organic containing oxidants such as isocyanurates.

The hydrophilic water-soluble polymers employed in the hair pre-treatment compositions of the present invention are desirably cationic modified polysaccharides or synthetic polymers, which carry a net cationic charge. The foregoing includes known industrial compounds, which are commercially available from cosmetic suppliers. These include, but are not limited to, guar hydroxypropyl trimonium chlorides (GHPTCs) such as JAGUAR® and AQUACAT® products commercially available from Aqualon Corporation (Wilmington, Del.); cationic modified cellulosics such as polyquaternium 10 (i.e., cellulose 2-(2-hydroxy-3-(trimethylammonio)propoxy)ethyl ether), one of a series of CELQUAT® products from Akzo Nobel (Amsterdam, Netherlands); and diallyl dimethyl ammonium chloride/acrylamide copolymer such as MERQUAT® products (e.g., (polyquaternium-7) commercially available from Nalco Company (Naperville, Ill.).

The charge density of the cationic polymers may be modified to balance substantivity with removal to avoid build-up on hair. The charge density, related to the amine functional cationic groups, is typically from about 0.01 meq/gram to 10 meq/gram, and preferably, from about 0.2 to about 7 meq/gram, and most preferably, between about 0.18 to about 0.36 meq/gram.

The cationic polymers, which can used alone or in combination, are typically employed at a total cationic polymer(s) level of from about 0.1 to about 10% by weight, and preferably from about 0.5 to about 6% by weight, and most preferably from about 1 to about 3% by weight.

The lipophilic nonionic polymers suitable for use in the present invention include, but are not limited to, the following classes of compounds: polyvinyl stearyl ethers commercially available under the trade designation GIOVAREZ® from Phoenix Chemical, Inc. (Sommerville, N.J.), PVP/eicosene copolymers commercially available under the trade designation GANEX® from International Specialty Products (Wayne, N.J.), and hydrogenated castor oil/sebacic acid copolymers commercially available under the trade designation CRODABOND® from Croda (Edison, N.J.), a di-behenyl imidazolinium product such as QUATERNIUM 91 from Croda.

The lipophilic nonionic polymers may be used alone or in combination to achieve optimal wash off/water resistance during use. The total level of lipophilic nonionic polymer(s) employed may be from about 1 to about 15% by weight, preferably, from about 2 to about 10% by weight, and most preferably, from about 4 to about 8% by weight.

The ratio of hydrophilic cationic polymer(s) to lipophilic nonionic polymer(s) may be from about 1:10 to about 10:1, and a preferred ratio is from about 1:7 to about 7:1 by weight in the final composition.

The oil-soluble antioxidants employed by the present invention include, but are not limited to, tocopherol (e.g., alpha tocopherol), tocotrienol (e.g., alpha tocotrienol), and carotenoids. The oil-soluble antioxidants, which can used alone or in combination with one another, are typically present at a total amount of oil-soluble antioxidant(s) of from about 0.1 to about 10% by weight of the formula, and preferably, at about 1 to about 5% by weight, and most preferably, from about 1 to about 3% by weight.

The water-soluble antioxidants suitable for use in the present invention include, but are not limited to, sulfur containing amino acids such as cysteine or methionine, their analogs, and di- or tri-peptides containing at least one cysteine or methionine moiety in the amino acid sequence; sodium thoisulfate; butylhydroxytoluene (BHT); butylhydroxyanisole (BHA); sodium bisulfate; sodium metabisulfite; and bis-phenol extracts of plant origin.

The water-soluble antioxidants may be used alone or in combination with one another. The water-soluble antioxidants are typically present in a total amount of one or more water-soluble antioxidants of from about 0.1 to about 5% by weight, and preferably, at about 1 to about 3% by weight in the finished product.

The above-described active ingredients may be incorporated in a cosmetic base, which exhibits both (i) compatibility with the above-described active ingredients, and (ii) acceptable aesthetics on the treated hair. The cosmetic base components may include, but are not limited to, deionized water; cationic surfactants; fatty alcohols such as cetearyl alcohol; nonionic emulsifiers; rheology modifiers; preservatives; chelators (e.g., EDTA and its salts, such as disodium EDTA); dyes; fragrances (e.g., mentha spicata, coconut, rose oil, sandlewood oil, etc.); pH control agents; and buffers. Humectants, such as glycerin and glycols (e.g., butylene glycol), and oils of mineral or plant origin may be used alone or in combination with any of the above-mentioned cosmetic base components as desired.

Exemplary cationic surfactants suitable for use in the present invention may include, but are not limited to, mono- and di- n-alkyl dimethyl ammonium chlorides, benzalkonium chlorides, and di-steary-di-methyl ammonium chloride. Exemplary fatty alcohols suitable for use in the present invention may include, but are not limited to, C10-C22 carbon chain alcohols (straight or branched), and stearyl alcohol. Exemplary nonionic emulsifiers suitable for use in the present invention may include, but are not limited to, sorbitan esters, ethoxylated fatty alcohols, and polysorbate 20, Exemplary rheology modifiers suitable for use in the present invention may include, but are not limited to, hydroxyalkyl celluloses, zanthan and guar gums, modified starches, and PEG 150 distearate. Exemplary preservatives suitable for use in the present invention may include, but are not limited to, 5-chloro-2-methyl-1,2-thiazol-3-one, 2-methyl-1,2-thiazol-3-one, 1,3-dimethylol-5,5-dimethylhydantoin, 3-iodo-2-propynyl butyl carbamate (e.g., KATHON™ CG commercially available from Sigma-Aldrich, Inc. (St. Louis, Mo.) and GLYDANT PLUS commercially available from Lonza, Ltd. (Basil, Switzerland)), and parabens such as methylparaben and propylparaben. Exemplary dyes suitable for use in the present invention may include, but are not limited to, FD&C AND D&C approved dyes such as D&C Yellow #10, Exemplary pH control agents suitable for use in the present invention may include, but are not limited to, citric acid, and potassium hydroxide. Exemplary buffer agents suitable for use in the present invention may include, but are not limited to, sodium phosphates, mono-, di-, and tribasic; and potassium citrates, mono-, di-, and tribasic. Exemplary oils of mineral or plant origin suitable for use in the present invention may include, but are not limited to, Johoba oil, Camellia Oleifera leaf extract, green tea extract and white tea extract.

The hair pre-treatment compositions of the present invention may comprise up to about 95% by weight of deionized water. Typically, deionized water is present in an amount of from about 45 to about 90% by weight, more typically, from about 65 to about 85% by weight, and even more typically, from about 65 to about 80% by weight, based on a total weight of the hair pre-treatment composition.

Other cosmetic base materials, such as any cationic surfactant, fatty alcohol, nonionic emulsifier, rheology modifier, preservative, chelator (e.g., EDTA or sodium salt thereof), dye, fragrance, pH control agent, buffer, humectants, and/or oil of mineral or plant origin may each independently be present in the hair pre-treatment compositions of the present invention in an amount of up to about 10% by weight, based on a total weight of the hair pre-treatment composition. Typically, each of the above-listed cosmetic base materials (other than deionized water), when present, are each independently present in an amount of from greater than 0 to about 5.0% by weight, more typically, from about 0.0001 to about 3.0% by weight, and even more typically, from about 0.01 to about 1.0% by weight, based on a total weight of the hair pre-treatment composition.

The pH of the resulting hair pre-treatment compositions typically ranges from about 4 to about 7, desirably ranging from about 4 to about 6, more desirably ranging from about 4 to about 5.

It should be noted that the hair pre-treatment compositions of the present invention may comprise, consist essentially of, or consist of any one the above-mentioned composition components or any combination of two or more of the above-mentioned composition components. In one exemplary hair pre-treatment composition of the present invention, the exemplary hair pre-treatment composition comprises (or consists essentially of, or consists of) at least one hydrophilic cationic polymer comprising guar hydroxypropyltrimonium chloride (GHPTC); at least one lipophilic nonionic polymer comprising (i) a polyvinyl stearyl ether, (ii) a vinylpyrrolidone-eicosene copolymer, or (iii) a combination of (i) and (ii); one or more water-soluble antioxidants or reducing agents comprising cysteine, methionine, or any mixture thereof; one or more oil-soluble antioxidants or reducing agents comprising a tocopherol, a tocotrienol, beta carotene, or any mixture thereof; and one or more of the following components: deionized water, cetearyl alcohol, PEG 40 castor oil, stearalkonium chloride, hydrogenated castor oil/sebacic acid copolymer, di-behenzyl imidazolinium, cetrimonium methosulfate, cetearyl alcohol, a polyoxyethylene ether of cetyl/stearyl alcohol, butylene glycol, isopropyl myristate, citric acid, an acrylate/aminoacrylate/C10-30 alkyl PEG-20 itaconate copolymer, trisodium EDTA, amidomethicone, cetrimonium chloride, 2-tridecoxyethanol, Camellia Oleifera leaf extract, Camellia Sinensis (White Tea) extract, methylchloroisothiazolinone, methylisothiazolinone, and a fragrance.

In another exemplary hair pre-treatment composition of the present invention, the exemplary hair pre-treatment composition comprises (or consists essentially of, or consists of) at least one hydrophilic cationic polymer comprising guar hydroxypropyltrimonium chloride (GHPTC); at least one lipophilic nonionic polymer comprising (i) a polyvinyl stearyl ether, (ii) a vinylpyrrolidone-eicosene copolymer, or (iii) a combination of (i) and (ii); one or more water-soluble antioxidants or reducing agents comprising cysteine, methionine, or any mixture thereof; one or more oil-soluble antioxidants or reducing agents comprising a tocopherol, a tocotrienol, beta carotene, or any mixture thereof; and all of the following components: deionized water, cetearyl alcohol, PEG 40 castor oil, stearalkonium chloride, hydrogenated castor oil/sebacic acid copolymer, di-behenzyl imidazolinium, cetrimonium methosulfate, cetearyl alcohol, a polyoxyethylene ether of cetyl/stearyl alcohol, butylene glycol, isopropyl myristate, citric acid, an acrylate/aminoacrylate/C10-30 alkyl PEG-20 itaconate copolymer, trisodium EDTA, amidomethicone, cetrimonium chloride, 2-tridecoxyethanol, Camellia Oleifera leaf extract, Camellia Sinensis (White Tea) extract, methylchloroisothiazolinone, methylisothiazolinone, and a fragrance.

It should be noted that the hair pre-treatment compositions of the present invention comprise, consist essentially of, or consist of one or more composition components, discussed above, that are not present in other hair treatment compositions, for example, shampoos and/or conditioners. In addition, the hair pre-treatment compositions of the present invention typically do not contain composition components found in shampoos and/or conditioners. Composition components that are typically found in shampoos and/or conditioners, but are not typically present in the hair pre-treatment compositions of the present invention, include, but are not limited to, anionic surfactants.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in—the art without departing from the spirit of the present invention and/or the scope of the appended claims.

EXAMPLES

Example 1

Composition and Preparation of Cosmetic Base

The following cosmetic base ingredients were mixed as described below.

| INGREDIENT | PERCENT WT/WT |
|---|---|
| Part A. WATER PHASE | |
| DEIONIZED WATER | 77.4999 |
| HYROXYETHYLCELLULOSE | 2.0000 |
| TRISODIUM EDTA | 0.5000 |
| GLYCERINE | 2.0000 |
| BUTYLENE GLYCOL | 2.0000 |
| AMIDOMETHICONE(and)CETRIMONIUM CHLORIDE(and)TRIDECETH 12 | 1.0000 |
| CITRIC ACID | 0.2000 |
| Part B. OIL PHASE | |
| STEARALKONIUM CHLORIDE | 6.0000 |
| CETEARYL ALCOHOL | 3.0000 |
| CETEARETH 20 | 3.0000 |
| ISOPROPYL PALMITATE | 1.0000 |
| MINERAL OIL | 1.0000 |
| PART C | |
| PRESERVATIVE (KATHON ™ CG) | 0.3000 |
| DYE AND FRAGRANCE (i.e., dye - FD&C RED 40, Orco Organic (E. Providence, RI), 0.0001 wt %; and fragrance - Belle-Aire #70330, Belle-Aire Fragrances (Mundelein, IL), 0.5000 wt %) | 0.5001 |

PROCEDURE:
1 - HEAT PART A TO 70° C. AND HOLD WITH AGITATION
2 - PRE-MELT PART B IN SEPARATE VESSEL AND HEAT TO 70° C.
3 - ADD PART B TO PART A WITH AGITATION
4 - COOL TO 35° C. AND ADD PART C IN ORDER
5 - ADJUST PH TO 5-6 WITH 50% CITRIC ACID IN DEIONIZED WATER

Example 2

Composition and Preparation of Protective Hair Pre-Treatment

The following hair pre-treatment composition components were mixed as described below.

| INGREDIENT | PERCENT WT/WT |
|---|---|
| A. WATER PHASE | |
| DEIONIZED WATER | 74.2999 |
| GUAR HYDROXYPROPYLTRIMONIUM CHLORIDE | 0.5000 |
| HYROXYETHYLCELLULOSE | 2.0000 |
| GREEN TEA EXTRACT | 1.0000 |
| CYSTEINE | 1.0000 |
| TRISODIUM EDTA | 0.5000 |
| GLYCERINE | 2.0000 |
| AMIDOMETHICONE(and)CETRIMONIUM CHLORIDE(and)TRIDECETH 12 | 1.0000 |
| CITRIC ACID | 0.2000 |
| B. OIL PHASE | |
| STEARALKONIUM CHLORIDE | 6.0000 |
| CETEARYL ALCOHOL | 3.0000 |
| CETEARETH 20 | 3.0000 |
| ISOPROPYL PALMITATE | 1.0000 |
| TOCOPHEROL | 1.0000 |
| POLYVINYL STEARYL ETHER | 2.0000 |
| MINERAL OIL | 1.0000 |
| PART C | |
| PRESERVATIVE (KATHON ™ CG) | 0.3000 |
| DYE AND FRAGRANCE) (i.e., dye - FD&C Blue #1, Orco Organic (E. Providence, RI), 0.0001 wt %; and fragrance - spearmint oil 50-6250-00, Lebermuth Company (South Bend, IN), 0.2000 wt %) | 0.2001 |

PROCEDURE
1 - HEAT PART A TO 70° C. AND HOLD WITH AGITATION
2 - PRE-MELT PART B IN SEPARATE VESSEL AND HEAT TO 70° C.
3 - ADD PART B TO PART A WITH AGITATION
4 - COOL TO 35° C. AND ADD PART C IN ORDER
5 - ADJUST PH TO 5-6 WITH 50% CITRIC ACID IN DEIONIZED WATER

Examples 3-7

The following examples consist of compositions made via the procedure outlined in Examples 1 and 2 above.

| INGREDIENT | PERCENT WT/WT EXAMPLE | | | | |
|---|---|---|---|---|---|
| | 3 | 4 | 5 | 6 | 7 |
| Guar Hydroxypropyltrimonium Chloride | 1.0 | — | 3.0 | — | 1.0 |
| Polyquaternium 10 | 2.0 | — | — | 5.0 | — |
| Polyquaternium 7 | — | 1.0 | — | 3.0 | — |
| Polyvinyl Stearyl Ether | 1.0 | 8.0 | 5.0 | — | 2.0 |
| PVP/Eicosene Copolymer | 8.0 | 4.0 | — | 1.0 | — |
| Hydrogenated Castor Oil/Sebacic Copolymer | — | — | — | — | 5.0 |
| Methionine | 0.5 | — | — | 0.1 | 2.0 |
| Cysteine | — | 3.0 | — | 2.5 | — |
| BHT | 0.1 | — | — | — | — |
| BHA | — | 2.0 | — | — | — |
| Sodium thiosulfate | 0.3 | — | — | — | — |
| Sodium metabisulfite | — | — | 1.0 | — | — |
| Sodium sulfite | — | 0.1 | — | — | — |
| Green tea extract | — | — | — | — | 1.0 |
| White tea extract | — | — | — | — | 1.0 |
| Polyphenols of plant origin[1] | — | — | 5.0 | — | — |
| Tocopherol | 0.1 | — | 0.5 | 1.0 | 0.5 |
| Tocotrienols | — | 0.3 | 1.0 | — | — |
| Beta Carotene | — | — | — | 2.0 | — |
| Cosmetic Base (from Example 1) | 87.0 | 81.6 | 84.5 | 85.4 | 87.5 |

[1]Resveratrol commercially available from Arch Corporation (South Plainfield, NJ).

Example 8

Method of Application

A series of six measurements were taken on swimmers after 2-4 hours immersion in a swimming pool in North Carolina. The object was to determine the efficacy regarding control of residual chlorine on swimmers hair with and without pre-treatment using the composition of example 7 in the foregoing examples. The composition of 7 above was applied to the hair and rinsed using tap water prior to swimming. The amount of product was judged in relation to length and fullness of the hair. The controls received no pre-treatment prior to pool immersion. The pool pH together with total and free chlorine was monitored using indicator strips during the measurements for consistency. Results are shown below.

| | AVERAGES OF SIX MEASUREMENTS | |
|---|---|---|
| Measurements | Control (no pre-treatment) | Pre-treated with Example 7 |
| Pool pH | 7.6 | 7.6 |
| Pool total chlorine | 3* | 3 |
| Pool free chlorine | 3 | 3 |
| Hair pH | 7.7 | 6.5 |
| Hair total chlorine | 1.6 | 0 |
| Hair free chlorine | 0.33 | 0 |

*Scale for chlorine analysis: 1 - low, 2 - moderate, 3 - high

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A method of protecting hair from oxidizing agents, said method comprising:
    pre-treating the hair with a hair pre-treatment composition comprising:
    from about 0.1 wt % to about 10 wt % of guar hydroxypropyltrimonium chloride (GHPTC);
    from about 1.0 wt % to about 15 wt % of a polyvinyl stearyl ether in combination with a hydrogenated castor oil/sebacic acid copolymer;
    one or more water-soluble antioxidants or reducing agents, the one or more water-soluble antioxidants or reducing agents comprising cysteine, methionine, or any mixture thereof; and one or more oil-soluble antioxidants or reducing agents, the one or more oil-soluble antioxidants or reducing agents comprising a tocopherol, a tocotrienol, beta carotene, or any mixture thereof.

2. Treated hair resulting from the method of claim 1.

3. A method of protecting hair from oxidizing agents, said method comprising:
pre-treating the hair with a hair pre-treatment composition comprising:
at least one lipophilic nonionic polymer comprising (i) a polyvinyl stearyl ether, (ii) a hydrogenated castor oil/sebacic acid copolymer, or (iii) a combination of (i) and (ii);
at least one hydrophilic cationic polymer comprising guar hydroxypropyltrimonium chloride (GHPTC), a cationic cellulosic polymer, a diallyl dimethyl ammonium chloride/acrylamide copolymer, or any combination thereof;
one or more water-soluble antioxidants or reducing agents comprising cysteine, methionine, BHT, BHA, a polyphenol of plant origin, or any mixture thereof; and
one or more oil-soluble antioxidants or reducing agents comprising a tocopherol, a tocotrienol, beta carotene, or any mixture thereof.

4. A method of protecting hair from oxidizing agents, said method comprising:
pre-treating the hair with a hair pre-treatment composition comprising:
from about 0.1 wt % to about 10 wt % of guar hydroxypropyltrimonium chloride (GHPTC); from about 1.0 wt % to about 15 wt % of a polyvinyl stearyl ether in combination with a hydrogenated castor oil/sebacic acid copolymer;
a water-soluble antioxidant or reducing agent comprising methionine; and
an oil-soluble antioxidant or reducing agent comprising a tocopherol.

5. The method according to claim 4, wherein the composition further comprises at least one cosmetic base material comprising a chelating agent for sequestering ionic metallic species encountered in a treated pool.

6. The method according to claim 1, wherein the hair pre-treatment composition comprises:
methionine; and
alpha tocopherol.

7. The method according to claim 6, wherein the hair pre-treatment composition further comprises deionized water, cetearyl alcohol, PEG 40 castor oil, stearalkonium chloride, di-behenyl imidazolinium, butylene glycol, isopropyl myristate, citric acid, and trisodium EDTA.

8. The method according to claim 7, wherein the hair pre-treatment composition comprises:
from about 45 wt % to about 90 wt % of deionized water;
from about 0.1 wt % to about 5 wt % of methionine;
from about 0.1 wt % to about 5 wt % of alpha tocopherol;
from greater than 0 to about 5.0 wt % of cetearyl alcohol;
from greater than 0 to about 5.0 wt % of PEG 40 castor oil;
from greater than 0 to about 5.0 wt % of stearalkonium chloride;
from greater than 0 to about 5.0 wt % of di-behenyl imidazolinium;
from greater than 0 to about 5.0 wt % of butylene glycol;
from greater than 0 to about 5.0 wt % of isopropyl myristate;
from greater than 0 to about 5.0 wt % of citric acid; and
from greater than 0 to about 5.0 wt % of trisodium EDTA.

9. The method according to claim 8, wherein the hair pre-treatment composition comprises:
about 10 wt % of guar hydroxypropyltrimonium chloride (GHPTC); and
from about 4 wt % to about 8 wt % of a polyvinyl stearyl ether in combination with a hydrogenated castor oil/sebacic acid copolymer.

10. The method according to claim 3, wherein the hair pre-treatment composition comprises:
methionine; and
alpha tocopherol.

11. The method according to claim 7, wherein the hair pre-treatment composition comprises:
from about 45 wt % to about 90 wt % of deionized water;
from about 4 wt % to about 8 wt % of a polyvinyl stearyl ether in combination with a hydrogenated castor oil/sebacic acid copolymer;
from about 0.1 wt % to about 5 wt % of methionine; and
from about 0.1 wt % to about 5 wt % of alpha tocopherol.

12. The method according to claim 11, wherein said method further comprises:
exposing the treated hair to an oxidizing environment; and
rinsing the treated hair prior to or after exposure to the oxidizing environment.

13. The method according to claim 12, wherein said method further comprises:
rinsing the treated hair prior to exposure the treated hair to the oxidizing environment.

14. The method according to claim 12, wherein said method further comprises:
shampooing the treated hair to remove at least a portion of the hair pre-treatment composition; and
conditioning the hair following or during the shampooing step.

15. The method according to claim 11, wherein the oxidizing environment comprises water within a chlorinated swimming pool.

16. The method according to claim 4, wherein the hair pre-treatment composition comprises:
from about 45 wt % to about 90 wt % of deionized water;
from about 0.1 wt % to about 5 wt % of methionine;
from about 0.1 wt % to about 5 wt % of alpha tocopherol;
from greater than 0 to about 5.0 wt % of cetearyl alcohol;
from greater than 0 to about 5.0 wt % of PEG 40 castor oil;
from greater than 0 to about 5.0 wt % of stearalkonium chloride;
from greater than 0 to about 5.0 wt % of di-behenyl imidazolinium;
from greater than 0 to about 5.0 wt % of butylene glycol;
from greater than 0 to about 5.0 wt % of isopropyl myristate;
from greater than 0 to about 5.0 wt % of citric acid;
from greater than 0 to about 5.0 wt % of trisodium EDTA; and
from greater than 0 to about 5.0 wt % of at least one of green tea extract and white tea extract.

17. The method according to claim 16, wherein the hair pre-treatment composition comprises:
about 10 wt % of guar hydroxypropyltrimonium chloride (GHPTC); and
from about 4 wt % to about 8 wt % of a polyvinyl stearyl ether in combination with a hydrogenated castor oil/sebacic acid copolymer.

18. The method according to claim 17, wherein said method further comprises:
rinsing the treated hair prior to exposure to an oxidizing environment.

19. The method according to claim 18, wherein said method further comprises:

shampooing the treated hair to remove at least a portion of the hair pre-treatment composition; and conditioning the hair following or during the shampooing step.

* * * * *